(12) United States Patent
Moshtagh

(10) Patent No.: US 9,764,032 B2
(45) Date of Patent: Sep. 19, 2017

(54) MULTI-VITAMIN KIDS GUMMIES HAVING BAOBAB AND METHOD OF MAKING THEREOF

(71) Applicant: Rozita Moshtagh, Carlsbad, CA (US)

(72) Inventor: Rozita Moshtagh, Carlsbad, CA (US)

( * ) Notice: Subject to any disclaimer, the term of this patent is extended or adjusted under 35 U.S.C. 154(b) by 213 days.

(21) Appl. No.: 14/733,968

(22) Filed: Jun. 9, 2015

(65) Prior Publication Data
US 2015/0265665 A1   Sep. 24, 2015

Related U.S. Application Data

(60) Provisional application No. 62/114,867, filed on Feb. 11, 2015.

(51) Int. Cl.
| | | |
|---|---|---|
| *A61K 36/00* | (2006.01) | |
| *A61K 45/06* | (2006.01) | |
| *A23G 3/36* | (2006.01) | |
| *A23G 3/44* | (2006.01) | |
| *A23G 3/48* | (2006.01) | |
| *A23L 21/12* | (2016.01) | |
| *A23L 33/15* | (2016.01) | |
| *A23L 25/00* | (2016.01) | |
| *A23L 33/155* | (2016.01) | |
| *A23L 33/16* | (2016.01) | |
| *A23L 33/175* | (2016.01) | |
| *A23L 29/281* | (2016.01) | |

(52) U.S. Cl.
CPC ............ *A61K 45/06* (2013.01); *A23G 3/368* (2013.01); *A23G 3/44* (2013.01); *A23G 3/48* (2013.01); *A23L 21/12* (2016.08); *A23L 25/30* (2016.08); *A23L 33/15* (2016.08); *A23L 33/155* (2016.08); *A23L 33/16* (2016.08); *A23L 33/175* (2016.08); *A23L 29/284* (2016.08)

(58) Field of Classification Search
None
See application file for complete search history.

(56) References Cited

U.S. PATENT DOCUMENTS 6,274,123 B1 *   8/2001   Pauly ................... A61K 8/97
424/59
2011/0313055 A1 *  12/2011   Ervin .................. A23G 3/40
514/777

OTHER PUBLICATIONS

Coe, Polyphenol content and in vitro bioaccessibility of six baobab fruit extracts. Proceedings of the Nutrition Society, (2012) vol. 71, Supp. OCE2. Abstract No. E26.*

* cited by examiner

*Primary Examiner* — Qiuwen Mi

(57) ABSTRACT

The embodiments herein relate to a multi-vitamin kids' gummies composition and a method of making the same. The multi-vitamin kids' gummies comprises a fruit powder, a thickening agent, a vitamin mix and water. The fruit powder is baobab fruit powder. The thickening agent is gelatine. The method of making multi-vitamin kids' gummies comprises mixing a predetermined amount of water and a predetermined amount of a thickening agent to obtain a mixture. The mixture is boiled to get a gel-like consistency. The mixture is cooled to room temperature. A predetermined amount of a fruit powder is added to the mixture. The fruit powder is baobab fruit powder. The mixture is kept at room temperature for at least 15 minutes and the mixture is molded to form gummies or candies.

5 Claims, 6 Drawing Sheets

MULTI-VITAMIN KIDS GUMMIES HAVING BAOBAB AND METHOD OF MAKING THEREOF

BACKGROUND

Technical Field of Invention

The embodiments herein generally relate to gummies for kids and particularly to multi-vitamin gummies. The embodiments herein more particularly relates to kids' gummies comprising baobab as a main source of vitamins and minerals and method of making the same.

Description of Related Art

Baobab is the common name for each of the nine species of tree in the genus *Adansonia. Adansonia digitata* is the most widespread of the *Adansonia* species on the African continent, found in the hot, dry savannahs of sub-Saharan Africa. English common names for the baobab include dead-rat tree (from the appearance of the fruits), monkey-bread tree (the soft, dry fruit is edible), upside-down tree (the sparse branches resemble roots) and cream of tartar tree (cream of tartar).

Baobab fruit has already exploded onto the markets in Asia and Europe, and is a prime new ingredient for the US market, given its unique functional health properties. Baobab fruit has a citrusy flavor and boasts more vitamins and minerals than found in oranges, bananas and even blackcurrants. In addition to its potent micronutrient profile, baobab has been confirmed to act as a prebiotic, and its high percentage of fiber by weight makes it a well-rounded ingredient for numerous food applications.

Baobab fruit (*Adansonia Digitata* L.) grows natively in Africa. Some baobab fruit trees are reported to be up to 1000 years of age and often times the tree is referred to as the "Ancient Tree of Life". The trunks can store greater than 30,000 gallons of water which help the trees survive long drought conditions. The fruit is found inside hard pods that hang upside down from the tree.

Traditionally, the baobab fruit is used to create a delicious, tangy health drink which is especially popular among pregnant women, children and the elderly. In various parts of East Africa, the dry fruit pulp is covered in sugary coating (usually with red coloring) and sold in packages as a sweet and sour candy called "umbuyu".

The seeds are mostly used as a thickener for soups, but may also be fermented into a seasoning, roasted for direct consumption, or pounded to extract oil. The tree also provides a source of fiber, dye, and fuel. The dry pulp is either eaten fresh or used to add to gruels on cooling after cooking—a good way of preserving the vitamin contents. In Tanzania, it is added to aid fermentation of sugar cane for beer making.

Among the various uses and various properties of baobab, it has never been used in making gummies or candies for children that could become an easiest and a rich source of vitamins and fibers for the children. Thus a need is felt to make use of the properties of baobab in making a rich and sweet multi-vitamin candies or gummies especially for the children.

The above mentioned shortcomings, disadvantages and problems are addressed herein, as detailed below.

SUMMARY OF THE INVENTION

Thus, the primary object of the embodiments herein is to provide a composition for multi-vitamin kids' gummies having baobab.

Another object of the embodiments herein is to provide a gummies or candies for kids having baobab as a main source of vitamin ingredients.

Yet another object of the embodiments herein is to provide a method of making gummies using baobab as a main source of vitamins, minerals and fibers.

The various embodiments herein disclose a multi-vitamin kids' gummies composition and a method of making the same.

According to one embodiment herein, the multi-vitamin kids' gummies comprises a fruit powder, a thickening agent, a vitamin mix and water. The fruit powder is baobab fruit powder. The thickening agent is gelatine. The fruit powder is in an amount of 5 mg. The thickening agent is in an amount of 1 mg. The water is in an amount of 5 ml.

According to another embodiment herein, the method of making multi-vitamin kids' gummies comprises mixing a predetermined amount of water and a predetermined amount of a thickening agent to obtain a mixture. The mixture is boiled to get a gel-like consistency. The mixture is cooled to room temperature. A predetermined amount of a fruit powder is added to the mixture. The fruit powder is baobab fruit powder. The mixture is kept at room temperature for at least 15 minutes and the mixture is molded to form gummies or candies.

The method further comprises adding a pre-mixed multivitamin mix for kids' to the mixture, according to another embodiment herein.

The method further comprises adding a coloring agent and a flavouring agent, according to another embodiment herein.

The predetermined amount of the fruit powder is 5 mg. The thickening agent is gelatin. The predetermined amount of the thickening agent 1 mg. The mixture has a pH of 8.

According to the embodiments herein, Baobab is used as multivitamin agent. Baobab is added to kid's multivitamin gummies to give it more "nutritional value" and "organic value" too in addition to a "premixed multivitamin".

According to another embodiment herein, baobab also possesses thickening agent properties; hence there is a lesser need of adding any thickening agent separately. Hence the gelatine added is in less proportion which has no nutritional value.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which:

FIGS. 2A, 2B, 2C, 2D and 2E are the comparative charts showing the contents of calcium, vitamin C, potassium, magnesium and zinc in baobab fruit and various other fruits, respectively, wherein FIG. 2A shows comparison chart of calcium content in baobab with various other fruits, wherein FIG. 2B shows comparison chart of vitamin C content in baobab with other fruits, wherein FIG. 2C shows comparison chart of potassium content in baobab with other fruits, wherein FIG. 2D shows comparison chart of magnesium content in baobab with other fruits, and wherein FIG. 2E shows comparison chart of zinc content in baobab with other fruits, according to the embodiments herein.

DETAILED DESCRIPTION OF THE DRAWINGS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments of the present invention provide a composition and a method of making gummies or candies using Baobab as a main source of vitamins and minerals.

According to one or more embodiments herein, a composition of multivitamin baobab candy or gummy comprises at least 0.2 weight percentage of gelatine and at least 0.1 weight percentage of baobab fruit powder in 5 ml of water. According to the embodiments herein, Baobab is used as multivitamin agent. Baobab is added to kid's multivitamin gummies to give it more "nutritional value" and "organic value" too in addition to a "premixed multivitamin". The premixed multivitamin is a mixture readily available in the market. Baobab fruit powder can be added to any such readily available mixture vitamin mixture.

According to another embodiment herein, baobab also possesses thickening agent properties; hence there is a lesser need of adding any thickening agent separately. Hence the gelatine added is in less proportion which has no nutritional value.

Figure 1:
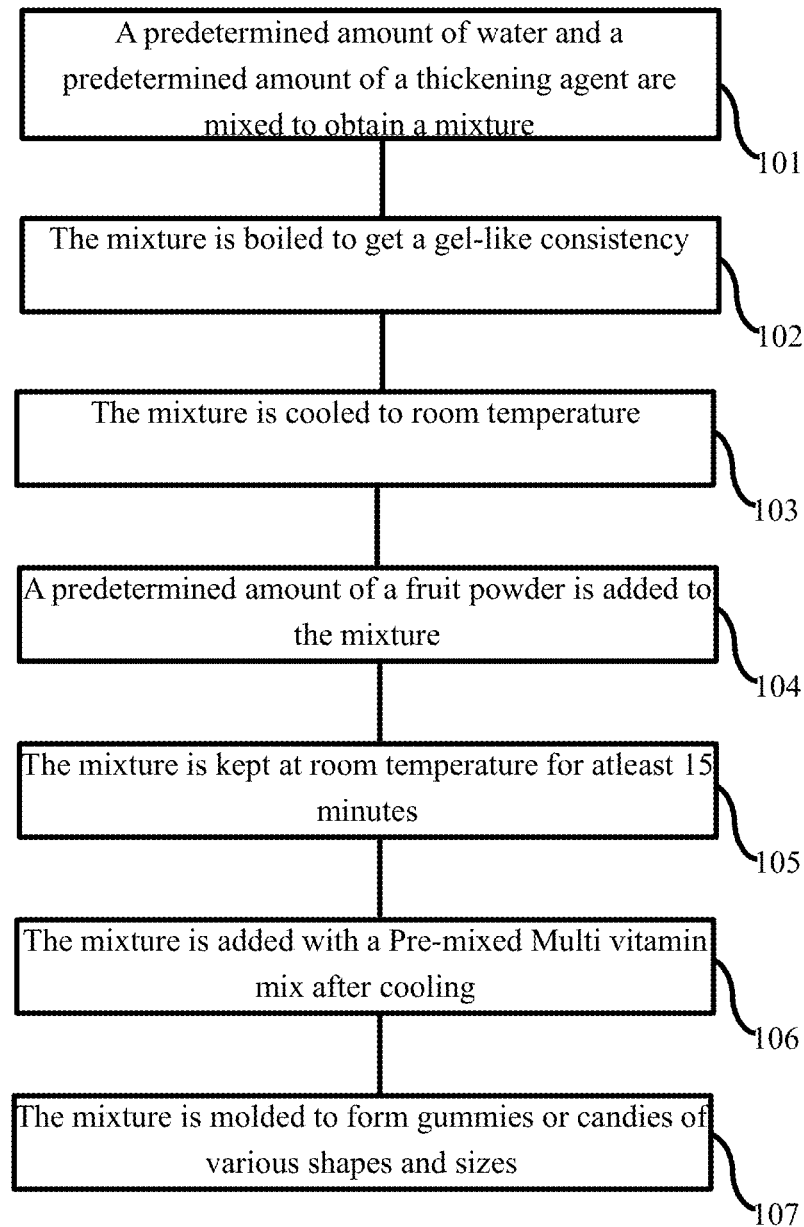
FIG. 1 is a flow chart showing the various steps involved in the method of making multi-vitamin kids' gummies, according to an embodiment herein.

FIG. 1 is a flow chart showing the various steps involved in the method of making multi-vitamin kids' gummies, according to an embodiment herein. With respect to FIG. 1, the method comprises mixing a predetermined amount of water and a predetermined amount of a thickening agent to obtain a mixture (101). The mixture is boiled to get a gel-like consistency (102). The mixture is cooled to room temperature (103). A predetermined amount of a fruit powder is added to the mixture (104). The mixture is kept at room temperature for at least 15 minutes (105). The mixture is added with a pre-mixed multivitamin mix for kids' to the mixture (106). The mixture is molded to form gummies or candies of various shapes and sizes (107). The fruit powder is baobab fruit powder. The method further comprises adding a coloring agent and a flavouring agent. The predetermined amount of the fruit powder is 5 mg. The thickening agent is gelatin. The predetermined amount of the thickening agent is 1 mg. The mixture has a pH of 8.

According to the embodiments herein, the addition of Baobab to the kids' multivitamin gummies makes the gummies more organic, natural and kosher (i.e. genuine and legitimate). The baobab powder adds more nutritional value to the multivitamin gummies and the usage of gel and other thickeners is reduced due to the addition of Baobab powder.

The Baobab Fruit was GRAS certified in 2009 (GRAS Notice No. GRN 000273).

The nutritional contents of Baobab fruit powder reported is shown in Table 1 below:

TABLE 1

| Nutritional value of Baobab fruit powder | |
|---|---|
| Antioxidants | >650/g ORAC |
| Calcium | 169 mg/100 g |
| Iron | 0.9 mg/100 g |
| Potassium | 2.7 g/100 g |
| Energy | >1087 kJ/100 g |
| Total Carbohydrates | 85.2 g/100 g |
| Protein | 2.1 g/100 g |
| Fat | 0.1 g/100 g |
| Total Dietary Fiber | 43.9 g/100 g |
| Total Soluble Fiber | 28.8 g/100 g |
| Total Sugar | 33.1 g/100 g |

Figure 2A:
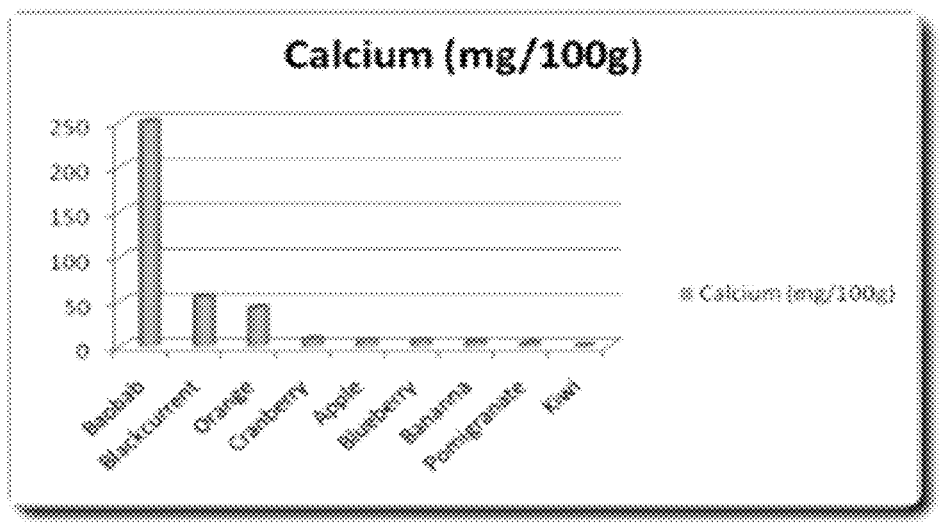
Figure 2B:
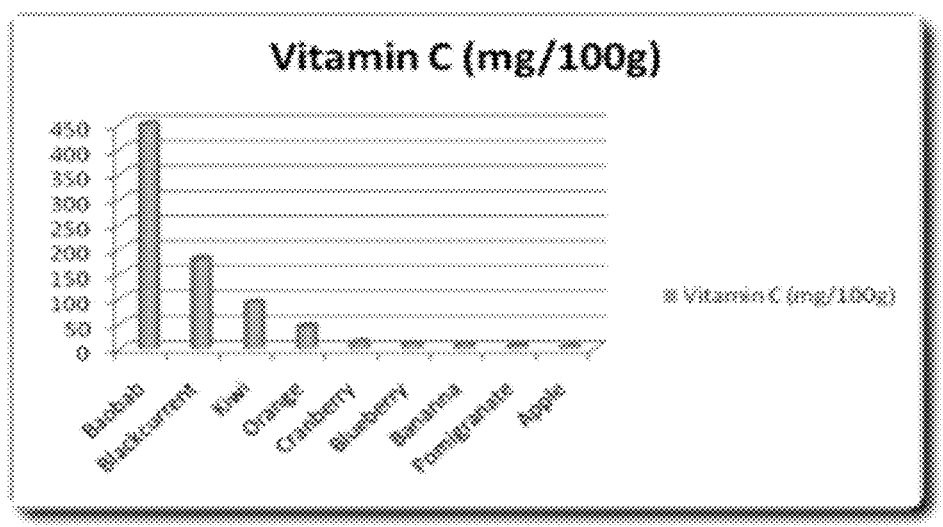
Figure 2C:
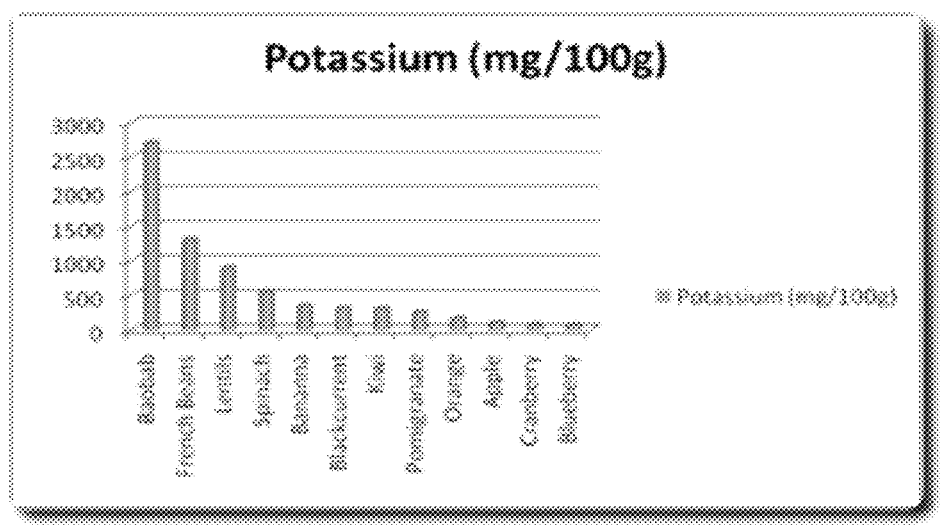
Figure 2D:
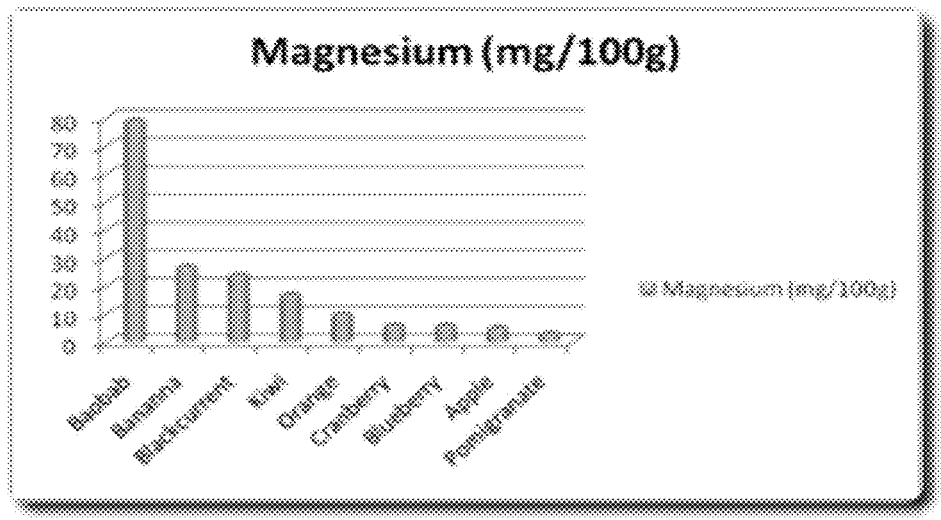
Figure 2E:
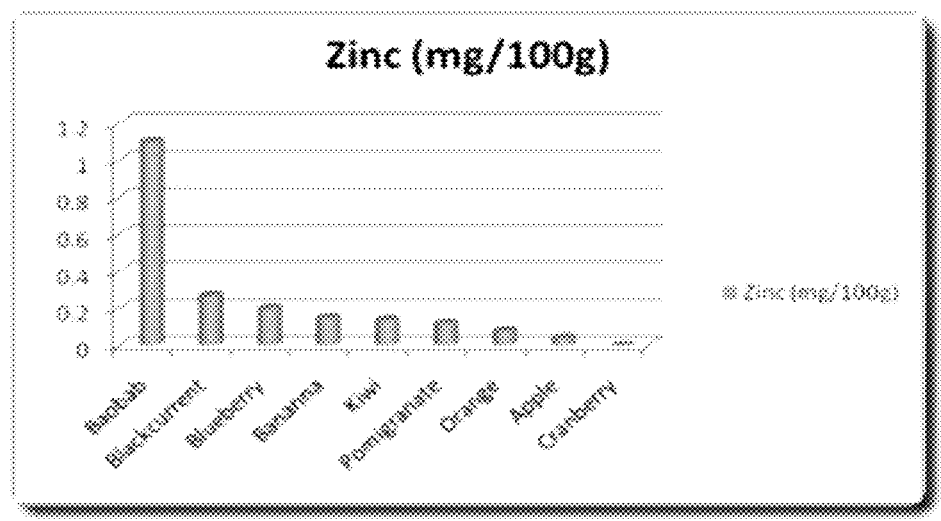

The baobab fruit powder has high vitamin and mineral content as compared to other commonly consumed fruits. FIGS. 2A, 2B, 2C, 2D and 2E are the comparative charts showing the contents of calcium, vitamin C, potassium, magnesium and zinc in baobab fruit and various other fruits, respectively, wherein FIG. 2A shows comparison chart of calcium content in baobab with various other fruits, wherein FIG. 2B shows comparison chart of vitamin C content in baobab with other fruits, wherein FIG. 2C shows comparison chart of potassium content in baobab with other fruits, wherein FIG. 2D shows comparison chart of magnesium content in baobab with other fruits, and wherein FIG. 2E shows comparison chart of zinc content in baobab with other fruits, according to the embodiments herein.

With respect to FIG. 2A, baobab is highly rich in calcium amounting to approximate 240 mg of calcium per 100 g of baobab powder while blackcurrant and orange are below the range of 50 mg/100 g of the powder. Calcium supports healthy bones and teeth, maintains regular muscle contractions, and blood clotting.

With respect to FIG. 2B, baobab is highly rich in vitamin C content amounting to approximate 440 mg of vitamin C per 100 g of powder while blackcurrant, kiwi and orange are below the range of 175 mg/100 g of powder. Vitamin C helps in protecting against immune system deficiencies, cardiovascular disease and even skin wrinkling.

With respect to FIG. 2C, baobab is rich in potassium content amounting to more than 2500 mg of potassium per 100 g of powder while French beans, lentils spinach and banana are below the range of 1500 mg/100 g of powder. Potassium helps in maintaining a healthy blood pressure.

With respect to FIG. 2D, baobab is rich in magnesium content amounting to more than 70 mg of magnesium per 100 g of powder while banana, black current and kiwi are below the range of 25 mg of magnesium per 100 g of powder. Magnesium supports muscle and nerve function, and bone strength.

With respect to FIG. 2E, baobab is rich in zinc content amounting to more than 1 mg of zinc per 100 g of powder while black current, blueberry and banana are below the range of 0.3 mg of zinc per 100 g of powders, respectively. Zinc is well known for its support of immunity.

According to one or more embodiments herein, the gummies or candies are the potent source of antioxidants. The gummies comprises Vitamin C, bioflavonoid and provitamin A.

According to one or more embodiments herein, the gummies or candies act as prebiotic because of the soluble fibers found in baobab fruit. The gummies exert prebiotic effects i.e. promote the growth of healthy bacteria in the gut—in vitro.

According to one or more embodiments herein, the gummies or candies are used as gastrointestinal aid. The baobab was traditionally used by African populations to support relief of diarrhoea, dysentery and constipation.

According to one or more embodiments herein, the gummies or candies act as natural excipients with good lubrificanting, binding-agent and diluting characteristics. Baobab has been used in some studies as hydrophilic excipients for the preparation of paracetamol and theophylline tablets. Baobab supports the creation of gel, acts as a thickening agent or a stabilizer, due to its soluble fiber content. Baobab acts as a natural preservative due to high vitamin C, potassium and phosphorus content.

Table 2 below shows a composition of the "premixed multivitamin" mixture according to an embodiment herein. The "premixed multivitamin" mixture used herein is any vitamin mixture readily available in the market.

TABLE 2 composition of "premixed multivitamin" mixture
Supplement Facts
Serving size: one (1) scoop (7.5 g)/30-day supply

| Amount per serving | | % Daily Value* |
|---|---|---|
| Calories | 15 | |
| Calories from fat | 0 g | 0% |
| Trans fat | 0 g | 0% |
| Potassium** (as Potassium citrate, Potassium Alginate) | 50 mg | 1% |
| Total Carbohydrates | 2 g | <1% |
| Dietary Fiber | <1 g | |
| Sugars (naturally occurring in Rice Protein) | <1 g | |
| Protein (from rice protein) | 2 g | 4% |
| Vitamin A (as vitamin A Palmitate) | 2,500 IU | 50% |
| Vitamin A (as Beta Carotene) | 3,500 IU | 70% |
| Vitamin C (as Ascorbic acid) | 500 mg | 833% |
| Vitamin D2 (as Ergocalciferol) | 250 IU | 62% |
| Vitamin E (as d-Alpha Tocopherol Succinate) | 200 IU | 666% |
| Vitamin K (As Phylloquinone) | 2.5 mg | 3% |
| Thiamine HCl (B-1) | 12.5 mg | 833% |
| Riboflavin (B-2) | 12.5 mg | 735% |
| Niacin (as Niacinamide) | 50 mg | 250% |
| Vitamin B-6 (as Pyridoxine HCl) | 12.5 mg | 625% |
| Folic Acid | 200 mcg | 50% |
| Vitamin B-12 (as Cyanocobalamin) | 12.5 mcg | 208% |
| Biotin (as d-Biotin) | 12.5 mcg | 4% |
| Pantothenic Acid (as d-Calcium Pantothenate) | 50 mg | 500% |
| Calcium** (as Dicalcium Phosphate, Calcium Carbonate) | 250 mg | 25% |
| Phosphorous** (As Dicalcium Phosphate) | 100 mg | 12% |
| Iodine (as Potassium Iodide) | 90 mcg | 60% |
| Magnesium**(as magnesium Carbonate) | 100 mcg | 12% |
| Zinc** (as Zinc Oxide) | 7.5 mcg | 100% |
| Selenium**(as Selenium Proteinate) | 25 mcg | 35% |
| Copper**(as Cupric Amino Acid Chelate) | 0.1 mg | 5% |
| Manganese**(as manganese Carbonate) | 2 mg | 100% |
| Chromium**(as Chromium Amino acid Chelate) | 25 mcg | 20% |
| Molybdenum**(as Molybdenum AA Chelate) | 25 mcg | 33% |
| Amino Acid profile: Naturally Occurring in Whole Protein | | |
| Alanine | 121 mg | + |
| Arginine | 194 mg | + |
| Aspartic Acid | 188 mg | + |
| Cystine/Cysteine | 46 mg | + |
| Glutamic Acid | 355 mg | + |

TABLE 2-continued composition of "premixed multivitamin" mixture
Supplement Facts
Serving size: one (1) scoop (7.5 g)/30-day supply

| Amount per serving | | % Daily Value* |
|---|---|---|
| Glycine*** | 98 mg | + |
| Histidine*** | 50 mg | + |
| Isoleucine*** | 88 mg | + |
| Leucine*** | 180 mg | + |
| Lysine*** | 73 mg | + |
| Methionine*** | 50 mg | + |
| Phenylalanine*** | 109 mg | + |
| Proline | 109 mg | + |
| Serine | 117 mg | + |
| Threonine*** | 75 mg | + |
| Tryptophan*** | 27 mg | + |
| Tyrosine | 111 mg | + |
| Valine*** | 98 mg | + |
| Also Contains: | | |
| Rice Bran | 500 mg | + |
| Lemon Bioflavonoids (lemon Fruit) | 200 mg | + |
| Lecithin (as Soy Lecithin) | 175 mg | + |
| Choline (as Choline Bitartrate and Lecithin) | 50 mg | + |
| Inositol | 50 mg | + |
| Hesperidin Complex (Citrus Fruit) | 12.5 mg | + |
| Para Amino Benzoic acid (PABA) | 12.5 mg | + |
| Rutin | 12.5 mg | + |
| In a base of: papain, Betain Hcl, Kelp | 3 mg | + |

*Percent Daily Values are based on a 2000 calorie diet
+ Daily value not established.
**Proteinate (Amino acid chelate)
***Essential Amino acids According to one or more embodiments herein, the gummies or candies are used in various applications. The various applications comprises bodybuilding/fitness supplements, vitamin/mineral formulas, smoothies, fruit juices, and powdered drinks, breakfast cereals and cereal bars, ice creams, yogurts and dairy products.

Example 1

5 ml of water and 1 mg of gelatine or any other thickening agent is mixed to form a mixture. The mixture is boiled till it gets a gel-like consistency. The mixture is kept for cooling at room temperature so that the temperature of the mixture drops to room temperature. 5 mg of Baobab powder is added and the mixture is kept for at least 15 minutes. A premixed "Vitamin Mix for kids", a colouring agent and a flavouring agent are added to the mixture. Then the mixture is poured into molds to make kids vitamin gummies in any or various or desired shape.

Any colour and flavour readily available in the market can be added, preferably, natural colours comprising fruit powders that make the gel colourful. Natural flavours that give the gummies more organic and natural quality.

Example 2

100 ml drink requires one teaspoon (4.6 grams) of baobab. Adding 50 g of the powder to a gallon of juice provides 25 g fiber (19 g of which is soluble fiber), 990 mg of potassium (32% of DV) and 73 mg of magnesium (23% of DV).

Example 3

Dense liquids such as smoothies, yogurt, ice cream or oatmeal absorb higher levels. As for energy bars, the rule of thumb is 6 g of Baobab powder per bar is added. It also works well in a yogurt coating.

Example 4

Mixing baobab powder with Reverse Osmosis water or any other distilled water by adding 1 ml of water to 1 mg of baobab powder then adding the "Premixed Multivitamin Mixture" to it.

The shelf life of baobab fruit powder is 24 months. Harvest time for baobab is February. Baobab is wild-harvested and as such cannot be certified organic, though in essence, it is. Finally, the product is sterilized by BI Nutraceuticals using our Protexx HP® steam sterilization. A fruit requires no processing while maintaining maximum nutrient potency and synergy. Baobab is not pasteurized, heat extracted, freeze dried or concentrated like so many other fruits. No nutrients are lost and the powder remains whole and unprocessed.

Baobab comprises more antioxidants than any other Superfruit, even acai, blueberries and pomegranate. Baobab is exceptionally rich in Fiber. More than half is ultra-healthful soluble fiber. Baobab can be used as raw whole food or in powdered form from the fruit. Baobab is planet's highest plant source of calcium. Baobab has more iron, potassium, magnesium and vitamin C than most of the other popular super foods. Baobab tastes great and is fun to eat.

Adequate levels of dietary fiber can help maintain a healthy digestive tract as well as lower in ammation. Baobab contains over 50% total dietary fiber-higher than all "Super fruits". The total fiber content is classified into two types i.e. soluble fiber which is 75% and insoluble fiber which is 25%. Pectin is one source of fiber in baobab and has been reported to have a role in reducing total and LDL Cholesterol. Pectin is also said to enhance the prebiotic bacteria in large intestine, potentially improving overall gut health. Baobab is reported to have pectin content of about 25 g per 100 g of fruit which may have a role in formulations as a gelling agent, a thickening agent or a stabilizer. Baobab's high pectin content makes it useful for products requiring thickening or binding.

The above descriptions about baobab show that it can be substituted in kid's multivitamin gummies instead of Pectin, Porcine gelatin, gelatin, Carnauba wax or bee wax.

Baobab's high nutrient content makes it the best ingredient in kid's multivitamin gummies as it is high in: antioxidants, fiber that acts like natural prebiotic and daily fiber source, vitamin c, calcium, magnesium and potassium (i.e. 6 times more than a banana).

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the claims.

I claim:

1. A multi-vitamin kids' gummies, comprises:
   a fruit powder, wherein the fruit powder is baobab fruit powder;
   a thickening agent, wherein the thickening agent is gelatin;
   a vitamin mix; and
   water, wherein the fruit powder is in an amount of 5 mg, the thickening agent is in an amount of 1 mg, and the water is in an amount of 5 ml.

2. A method of making multi-vitamin kids' gummies according to the composition of claim 1, comprises:
   mixing a predetermined amount of water and a predetermined amount of a thickening agent to obtain a mixture;
   boiling the mixture to get a gel-like consistency;
   cooling the mixture to room temperature;
   adding a predetermined amount of a fruit powder to the mixture, wherein the fruit powder is baobab fruit powder;
   keeping the mixture for at least 15 minutes; and
   molding the mixture to form the gummies.

3. The method as claimed in claim 2, wherein the method further comprises adding a pre-mixed multivitamin mix for kids' to the mixture, wherein the pre-mixed multivitamin mix for kids' is any vitamin mixture readily available in a market.

4. The method as claimed in claim 2, wherein the method further comprises adding a colouring agent and a flavouring agent.

5. The method as claimed in claim 2, wherein the mixture has a pH of 8.

* * * * *